United States Patent
Obata et al.

(10) Patent No.: US 10,340,868 B2
(45) Date of Patent: Jul. 2, 2019

(54) AMPLIFIER CIRCUIT INCLUDING FIRST INPUT BRANCH CIRCUIT, SECOND INPUT BRANCH CIRCUIT, FEEDBACK CAPACITOR, AND OPERATIONAL AMPLIFIER AND PULSE-WAVE MEASURING DEVICE

(71) Applicant: Panasonic Intellectual Property Management Co., Ltd., Osaka (JP)

(72) Inventors: Koji Obata, Osaka (JP); Kazuo Matsukawa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 259 days.

(21) Appl. No.: 15/594,075

(22) Filed: May 12, 2017

(65) Prior Publication Data

US 2017/0346457 A1 Nov. 30, 2017

(30) Foreign Application Priority Data

May 26, 2016 (JP) .................. 2016-105504

(51) Int. Cl.
*H03F 3/45* (2006.01)
*A61B 5/024* (2006.01)
(Continued)

(52) U.S. Cl.
CPC ..... *H03F 3/45475* (2013.01); *A61B 5/02108* (2013.01); *A61B 5/02427* (2013.01);
(Continued)

(58) Field of Classification Search
CPC ........................................................ H03F 3/45
(Continued)

(56) References Cited

U.S. PATENT DOCUMENTS

| 4,404,525 | A |   | 9/1983 | Amir et al. |
| 6,031,480 | A | * | 2/2000 | Soenen ............... H03F 3/45479 330/9 |

(Continued)

FOREIGN PATENT DOCUMENTS

| JP | 57-117832 | 7/1982 |
| JP | 57-159105 | 10/1982 |

(Continued)

*Primary Examiner* — Henry Choe
(74) *Attorney, Agent, or Firm* — McDermott Will & Emery LLP

(57) ABSTRACT

An amplifier circuit includes a first input branch circuit including a first sampling capacitor, a second input branch circuit including a second sampling capacitor, an averaging capacitor, and a subtraction capacitor, a feedback capacitor, and an operational amplifier. The first sampling capacitor samples an input voltage in a first time period and outputs a first voltage. The second sampling capacitor samples the input voltage in the first time period and outputs a second voltage. The averaging capacitor takes an average of the second voltage in the second time period and outputs a third voltage. The subtraction capacitor receives the third voltage in the first time period. The subtraction capacitor subtracts the first voltage from the third voltage and outputs a fourth voltage in the second time period. The operational amplifier is connected to the feedback capacitor and amplifies the fourth voltage. The first and second time periods are repeated alternately.

6 Claims, 5 Drawing Sheets

(51) Int. Cl.
  *A61B 5/00*    (2006.01)
  *A61B 5/021*   (2006.01)
(52) U.S. Cl.
  CPC .. *A61B 5/7225* (2013.01); *H03F 2203/45514* (2013.01); *H03F 2203/45551* (2013.01)
(58) Field of Classification Search
  USPC .................................... 330/9; 327/124, 307
  See application file for complete search history.

(56) References Cited

U.S. PATENT DOCUMENTS

| | | | | |
|---|---|---|---|---|
| 7,629,838 B2* | 12/2009 | Lim | ........................ | H03F 3/005 |
| | | | | 330/9 |
| 7,639,074 B2* | 12/2009 | Chen | ........................ | H03F 3/005 |
| | | | | 330/86 |
| 8,390,372 B2* | 3/2013 | Buter | ........................ | H03F 3/005 |
| | | | | 330/9 |
| 2006/0033561 A1* | 2/2006 | Perdoor | .................... | H03F 1/02 |
| | | | | 330/9 |

FOREIGN PATENT DOCUMENTS

| | | |
|---|---|---|
| JP | 58-216037 | 12/1983 |
| JP | 2000-022500 | 1/2000 |
| JP | 2010-177791 | 8/2010 |
| JP | 2011-171883 | 9/2011 |
| JP | 2013-094482 | 5/2013 |

* cited by examiner

AMPLIFIER CIRCUIT INCLUDING FIRST INPUT BRANCH CIRCUIT, SECOND INPUT BRANCH CIRCUIT, FEEDBACK CAPACITOR, AND OPERATIONAL AMPLIFIER AND PULSE-WAVE MEASURING DEVICE

BACKGROUND

1. Technical Field

The present disclosure relates to an amplifier circuit that amplifies a given signal and a pulse-wave measuring device using the amplifier circuit.

2. Description of the Related Art

Changes in the pressure or volume of peripheral blood vessels observed in accordance with the heart beat are measured. The measurement result is referred to as a pulse wave and is used for pulse rate measurement and the like. In a known measurement technique, light from a light source such as a light emitting diode (LED) is emitted onto a living body, reflected light or transmitted light is converted into current by a photodetector such as a photodiode, and the current is measured.

The current is converted to a voltage with a current-voltage conversion circuit, the analog value of the converted voltage is converted to a digital value by an analog-to-digital converter (hereinafter, referred to as an A/D converter) or another device, and a resultant signal is processed. The current converted by the photodetector has a constant direct-current component on which an alternating-current component that varies depending on vasoconstriction or other factors is superposed. Generally, since the voltage change in the alternating-current component is small compared with the resolution of the A/D converter, an amplifier circuit is inserted between the current-voltage conversion circuit and the A/D converter to amplify a signal. At this time, amplifying the direct-current component and the alternating-current component simultaneously might lead to voltage saturation and loss of the alternating-current component. To improve signal detectivity, it is important to not only adjust the intensity of the light source to an intensity suitable for an optimum amount of light, but also the amplification factor of the amplifier circuit.

An amplifier circuit in the related art includes resistors, capacitors, and an operational amplifier. The amplifier circuit hardly amplifies a direct-current component and amplifies substantially only an alternating-current component (for example, see Japanese Unexamined Patent Application Publication No. 57-117832).

SUMMARY

In one general aspect, the techniques disclosed here feature an amplifier circuit including a first input branch circuit, a second input branch circuit, a feedback capacitor, and an operational amplifier. The first input branch circuit includes a first sampling capacitor that, in operation, samples an input voltage in a first time period and outputs a first voltage. The second input branch circuit includes a second sampling capacitor, an averaging capacitor, and a subtraction capacitor. The second sampling capacitor, in operation, samples the input voltage in the first time period and outputs a second voltage. The averaging capacitor, in operation, takes an average of the second voltage in the second time period and outputs a third voltage. The subtraction capacitor, in operation, receives the third voltage in the first time period. The subtraction capacitor, in operation, subtracts the first voltage from the third voltage and outputs a fourth voltage in the second time period. The operational amplifier is connected to the feedback capacitor and, in operation, amplifies the fourth voltage. The first time period and the second time period are repeated alternately.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
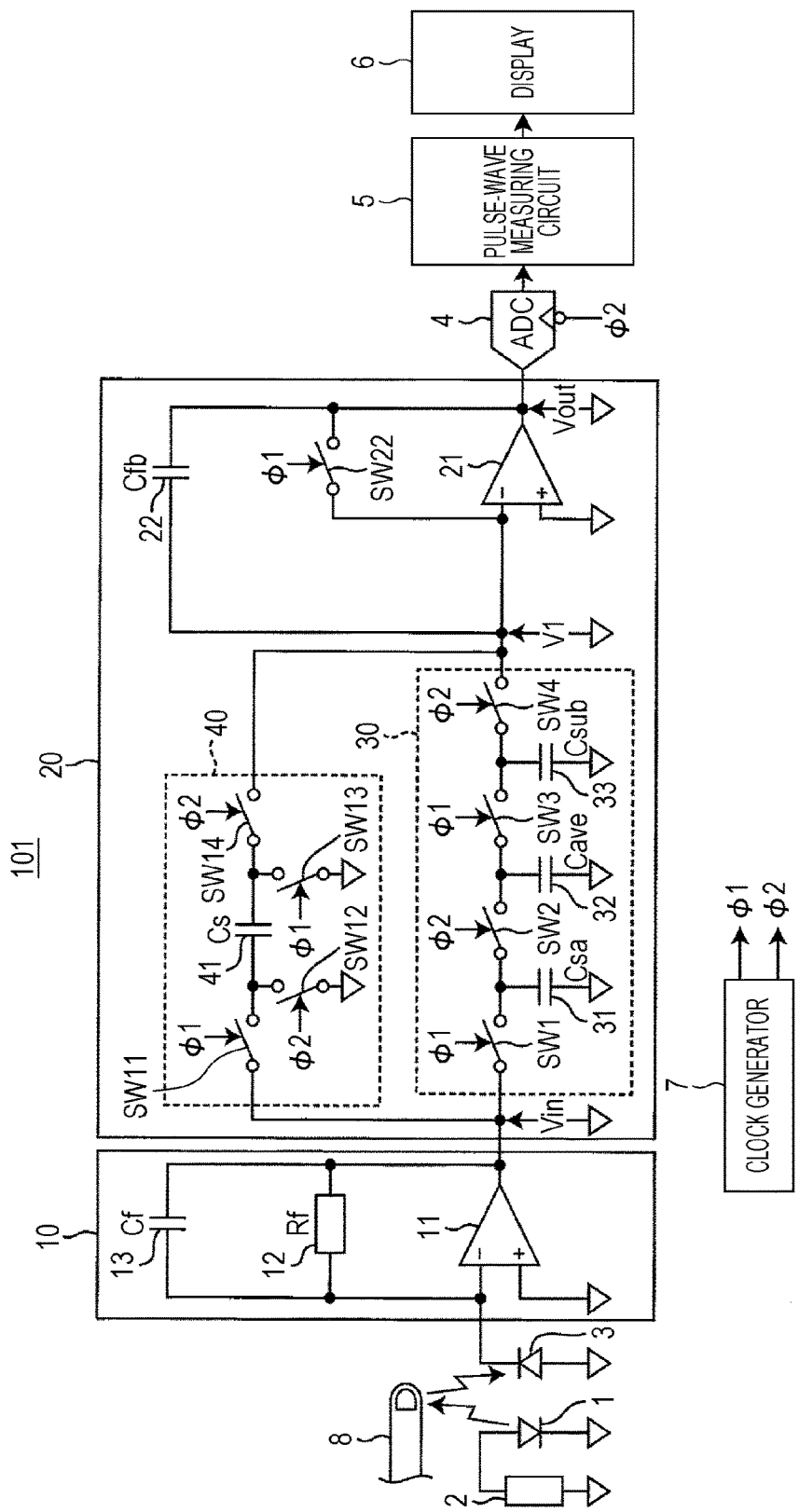
FIG. 1 is a circuit diagram illustrating a configuration example of a blood-vessel pulse-wave measuring device according to Embodiment 1.

However, since the amplifier circuit in Japanese Unexamined Patent Application Publication No. 57-117832 is a continuous-time circuit including resistors and capacitors, the amplifier circuit is difficult to operate intermittently and has high power consumption.

The amplifier circuit according to an aspect of the present disclosure can be operated intermittently and can be operated with lower power consumption than that in the related art.

The present disclosure includes at least an amplifier circuit and a pulse-wave measuring device according to the following aspects.

An amplifier circuit according to a first aspect includes:

a first input branch circuit including a first sampling capacitor that, in operation, samples an input voltage in a first time period and outputs a first voltage;

a second input branch circuit including a second sampling capacitor, an averaging capacitor, and a subtraction capacitor, the second sampling capacitor, in operation, sampling the input voltage in the first time period and outputting a second voltage, the averaging capacitor, in operation, taking an average of the second voltage in the second time period and outputting a third voltage, the subtraction capacitor, in operation, receiving the third voltage in the first time period, the subtraction capacitor, in operation, subtracting the first voltage from the third voltage and outputting a fourth voltage in the second time period;

a feedback capacitor; and an operational amplifier that is connected to the feedback capacitor and, in operation, amplifies the fourth voltage, wherein the first time period and the second time period are repeated alternately.

According to a second aspect, the amplifier circuit according to the first aspect may further include:

an offset capacitor inserted between the second input branch circuit and an input terminal of the operational amplifier; and a first offset switch that is inserted between a ground and a connection between the second input branch circuit and the offset capacitor, is switched on in the first time period, and is switched off in the second time period, wherein a noninverting input terminal of the operational amplifier is grounded.

According to a third aspect, the amplifier circuit according to the second aspect may further include:

a second offset switch that is inserted between an output terminal of the operational amplifier and the feedback capacitor, is switched off in the first time period, and is switched on in the second time period; and a third offset switch that is inserted between the feedback capacitor and the ground, is switched on in the first time period, and is switched off in the second time period.

According to a fourth aspect, in the amplifier circuit according to any one of the first to the third aspects, a capacitance value of the first sampling capacitor may be set to be equal to a total capacitance value of the second sampling capacitor, the averaging capacitor, the subtraction capacitor, and the feedback capacitor, the second sampling capacitor, the averaging capacitor, and the subtraction capacitor are connected together in series, and the feedback capacitor is connected to the second sampling capacitor, the averaging capacitor, and the subtraction capacitor in parallel.

According to a fifth aspect, in the amplifier circuit according to any one of the first to the third aspects, a capacitance value of the first sampling capacitor may be set to be equal to a total capacitance value of the second sampling capacitor, the subtraction capacitor, and the feedback capacitor, the second sampling capacitor and the subtraction capacitor are connected together in series, and the feedback capacitor is connected to the second sampling capacitor and the subtraction capacitor in parallel.

A pulse-wave measuring device according to a sixth aspect includes:

a light source;

a photodetector that, in operation, detects light from a target and outputs current;

a current-voltage conversion circuit that, in operation, converts the current to a voltage and outputs the voltage;

an amplifier circuit that, in operation, amplifies the voltage output by the current-voltage conversion circuit at a discrete time and outputs an analog voltage; and an analog-to-digital converter that, in operation, converts the analog voltage to a digital voltage, wherein:

the amplifier circuit includes a first input branch circuit including a first sampling capacitor that, in operation, samples the voltage output by the current-voltage conversion circuit in a first time period and outputs a first voltage, a second input branch circuit including a second sampling capacitor, an averaging capacitor, and a subtraction capacitor, the second sampling capacitor, in operation, sampling the voltage output by the current-voltage conversion circuit in the first time period and outputting a second voltage, the averaging capacitor, in operation, taking an average of the second voltage in the second time period and outputting a third voltage, the subtraction capacitor, in operation, receiving the third voltage in the first time period, the subtraction capacitor, in operation, subtracting the first voltage from the third voltage and outputting a fourth voltage in the second time period, a feedback capacitor, and an operational amplifier that is connected to the feedback capacitor and, in operation, amplifies the fourth voltage, and the first time period and the second time period are repeated alternately.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or a large scale integration (LSI) circuit. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a read-only memory (ROM), an optical disk or a hard disk drive, and when the software is executed by a processor, the software causes the processor together with peripheral devices to execute the functions specified in the software. A system or apparatus may include such one or more non-transitory recording median on which the software is recorded and a processor together with necessary hardware devices such as an interface.)

Hereinafter, embodiments according to the present disclosure will be described with reference to the drawings. Note that the same components are denoted by the same reference numerals in each embodiment below.

Embodiment 1

FIG. 1 is a circuit diagram illustrating a configuration example of a pulse-wave measuring device 101 according to Embodiment 1. In FIG. 1, the pulse-wave measuring device 101 includes a light emitting diode 1, a power supply circuit 2, a photodiode 3, a current-voltage converter circuit 10, an amplifier circuit 20, an A/D converter 4, a pulse-wave measuring circuit 5, a display 6, and a clock generator 7. The amplifier circuit 20 is a discrete-time amplifier circuit.

In FIG. 1, the light emitting diode 1 that is a light source is driven by supplying a power supply voltage from the power supply circuit 2. Light emitted from the light emitting diode 1 is reflected from or transmitted through, for example, a finger 8 of a person. The light reflected from or transmitted through the finger 8 is received by the photodiode 3 that is a photodetector. When the light is received by the photodiode 3, a predetermined current flows through the photodiode 3. The current is converted to a voltage by the current-voltage converter circuit 10, and the voltage is input to the amplifier circuit 20. The amplifier circuit 20 samples at least one input voltage Vin at discrete times, amplifies the input voltage Vin, and outputs, to the A/D converter 4, an output voltage Vout resulting from the amplification. The A/D converter 4 converts the analog value of the output voltage Vout to a digital voltage value and thereafter outputs the output voltage Vout to the pulse-wave measuring circuit 5. Based on the input digital voltage value, the pulse-wave measuring circuit 5 performs measurement of the pulse wave of a blood vessel with a publicly known pulse-wave measurement method disclosed in, for example, Japanese Unexamined Patent Application Publication No. 2013-094482 and outputs the pulse wave to, for example, the display 6. The display 6 displays the pulse wave form.

The current-voltage converter circuit 10 includes a parallel circuit composed of an operational amplifier 11, a resistor 12, and a capacitor 13. The resistor 12 and the capacitor 13 form a feedback circuit. The resistor 12 has a resistance value Rf, and the capacitor 13 has a capacitance value Cf. The noninverting input terminal of the operational amplifier 11 is grounded. Grounding may be performed at 0 volts (V) or at a predetermined voltage. The current-voltage converter circuit 10 converts current that is input to the inverting input terminal of the current-voltage converter circuit 10 to a voltage corresponding to the current and outputs the voltage from the output terminal thereof.

The amplifier circuit 20 is composed of a switched capacitor circuit in which an input voltage is amplified at discrete times. Specifically, the amplifier circuit 20 includes two input branch circuits 30 and 40 connected parallel to each other, an operational amplifier 21, a reset switch SW22, and a feedback capacitor 22. The reset switch SW22 and the feedback capacitor 22 form a feedback circuit. The parallel circuit composed of the input branch circuits 30 and 40 is connected between the input terminal of the amplifier circuit 20 and the inverting input terminal of the operational amplifier 21. The noninverting input terminal of the operational amplifier 21 is grounded. The input branch circuit 30 and the input branch circuit 40 respectively correspond to a second input branch circuit and a first input branch circuit in the present disclosure.

The input branch circuit 30 includes
(1) four switches SW1, SW2, SW3, and SW4 that are connected in series,
(2) a sampling capacitor 31 that is connected between the ground and the connection between the switch SW1 and the switch SW2, has a capacitance value Csa, and samples the input voltage Vin,
(3) an averaging capacitor 32 that is connected between the ground and the connection between the switch SW2 and the switch SW3, has a capacitance value Cave, and takes an average of the sampled voltage, and
(4) a subtraction capacitor 33 that is connected between the ground and the connection between the switch SW3 and the switch SW4, has a capacitance value Csub, subtracts a voltage sampled by a sampling capacitor 41 (described later) from the average voltage, and outputs a voltage resulting from the subtraction. The sampling capacitor 31 corresponds to a second sampling capacitor in the present disclosure.

The input branch circuit 40 includes
(1) a series circuit composed of a switch SW11, the sampling capacitor 41 having a capacitance value Cs, and a switch SW14 each of which is connected in series,
(2) a switch SW12 connected between the ground and the connection between the switch SW11 and the sampling capacitor 41, and
(3) a switch SW13 connected between the ground and the connection between the switch SW14 and the sampling capacitor 41. The sampling capacitor 41 is provided to sample the input voltage Vin. The sampling capacitor 41 corresponds to a first sampling capacitor in the present disclosure.

The clock generator 7 generates clock signals $\phi 1$ and $\phi 2$ having a mutual phase inversion relationship and, for example, a 50% duty cycle and outputs the clock signals $\phi 1$ and $\phi 2$ to the switches SW1, SW2, SW3, SW14, SW11, SW12, SW13, SW14, and SW22 in the amplifier circuit 20. The clock signal $\phi 1$ is applied as a control signal to the switches SW1, SW3, SW11, SW13, and SW22, and the clock signal $\phi 2$ is applied as a control signal to the switches SW2, SW4, SW12, and SW14. In a period when the clock signal $\phi 1$ and the clock signal $\phi 2$ are at a high level and at a low level, respectively (hereinafter, referred to as a first time period), the switches SW1, SW3, SW11, SW13, and SW22 are on, and the switches SW2, SW4, SW12, and SW14 are off. In a period when the clock signal $\phi 2$ and the clock signal $\phi 1$ are at the high level and at the low level, respectively (hereinafter, referred to as a second time period), the switches SW2, SW4, SW12, and SW14 are on, and the switches SW1, SW3, SW11, SW13, and SW22 are off. Note that the first time period and the second time period are alternately repeated.

In the amplifier circuit 20 configured as described above, when the clock signal $\phi 1$ is first at the high level, the sampling capacitors 31 and 41 sample the input voltage Vin and are charged in accordance with the input voltage Vin.

Subsequently, when the clock signal $\phi 2$ is at the high level, the charges of the sampling capacitor 31 are transferred to the averaging capacitor 32 via the switch SW2. At this time, the switches SW2 and SW3 are switched on and off, respectively, and charges stored in the averaging capacitor 32 are averaged. In contrast, a voltage corresponding to the charges stored in the sampling capacitor 41 is transferred to and received by the subtraction capacitor 33.

Further, when the clock signal $\phi 1$ is at the high level, the charges in the averaging capacitor 32 are transferred to the subtraction capacitor 33 via the switch SW3.

Subsequently, when the clock signal $\phi 2$ is at the high level, the subtraction capacitor 33 generates a voltage corresponding to charges obtained by subtracting the charges stored in the sampling capacitor 41 from the charges stored in the averaging capacitor 32, and the subtraction capacitor 33 outputs the voltage to the inverting input terminal of the operational amplifier 21. When the clock signal $\phi 1$ is at the high level, the output terminal and the input terminal of the operational amplifier 21 are connected to each other. After the output terminal and the input terminal are reset, and when the clock signal $\phi 2$ is at the high level, the operational amplifier 21 amplifies an input voltage V1 and outputs the amplified output voltage Vout.

In the amplifier circuit 20, the input branch circuit 40 is a circuit that samples the input voltage Vin and outputs the sampled voltage. The input branch circuit 30 is a circuit that samples the input voltage Vin, takes an average, subtracts the voltage sampled in the input branch circuit 40 from the average voltage, and outputs a voltage resulting from the subtraction.

A transfer function H of the amplifier circuit 20 in FIG. 1 is expressed in accordance with the following formula.

$$H = \frac{Vout}{Vin} = \frac{Cs}{Cfb} - \frac{Csa}{Cfb} \times \frac{Cave \times Csub}{(Csa + Cave) \times (Cave + Csub) \times z^1 - Cave^2} \quad (1)$$

As clear from Formula (1), the transfer function H of the amplifier circuit 20 is determined based on the capacitance values and the clock frequencies of the respective capacitors 31, 32, 33, 41, and 22.

In a case of gain H=1 in a direct current (z=1), the following formula is obtained from Formula (1).

$$1 = \frac{Cs}{Cfb} - \frac{Csa}{Cfb} \times \frac{Cave \times Csub}{(Csa + Cave) \times (Cave + Csub) - Cave^2} \quad (2)$$

From Formula (2), a capacitance value Cfb is expressed in accordance with the following formula.

$$Cfb = Cs - Csa \times \frac{Cave \times Csub}{(Csa + Cave) \times (Cave + Csub) - Cave^2} \quad (3)$$

From Formula (3), the capacitance value Cs is expressed in accordance with the following formula.

$$Cs = Cfb + Csa \times \frac{Cave \times Csub}{(Csa + Cave) \times (Cave + Csub) - Cave^2} \quad (4)$$

$$= Cfb + \frac{Csa \times Cave \times Csub}{Csa \times Cave + Csa \times Csub + Cave \times Csub}$$

As clear from Formula (4), the capacitance value Cs of the sampling capacitor 41 can be set as a total capacitance of the capacitor 22 having the capacitance value Cfb and the capacitors 31, 32, and 33 having the capacitance values Csa, Cave, and Csub, respectively. The capacitors 31, 32, and 33 are connected together in series, and the capacitor 22 is connected to the capacitors 31, 32, and 33 in parallel.

If Cave>>(Csa×Csub), the capacitance value Cs of the sampling capacitor 41 is expressed in accordance with the following formula.

$$Cs = Cfb + \frac{Csa \times Csub}{Csa + \frac{Csa \times Csub}{Cave} + Csub} \quad (5)$$

$$\approx Cfb + \frac{Csa \times Csub}{Csa + Csub}$$

As clear from Formula (5), the capacitance value Cs of the sampling capacitor 41 can be set as a total capacitance of the capacitor 22 having the capacitance value Cfb and the capacitors 31 and 33 having the capacitance values Csa and Csub, respectively. The capacitors 31 and 33 are connected together in series, and the capacitor 22 is connected to the capacitors 31 and 33 in parallel.

An example frequency characteristic of the gain of the amplifier circuit 20 in FIG. 1 will be described.

Figure 4:
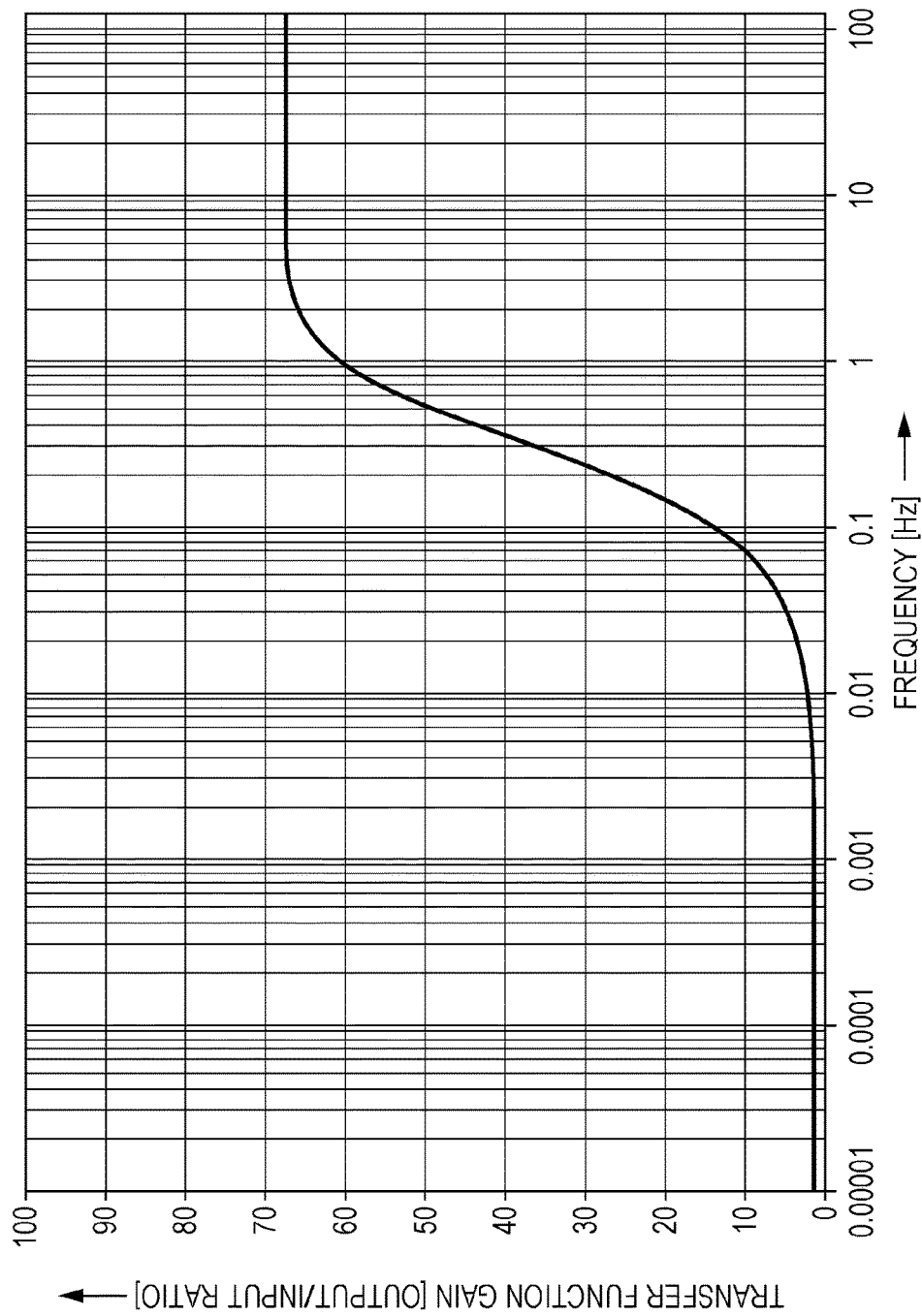
FIG. 4 is a graph illustrating the frequency characteristics of the gain observed when the discrete-time amplifier circuit in FIG. 1 has a 256 Hz clock frequency.

FIG. 4 is a graph illustrating the frequency characteristics of the gain observed when the amplifier circuit 20 in FIG. 1 has a 256 Hz clock frequency. As clear from FIG. 4, in the amplifier circuit 20, the direct-current component is hardly amplified with, for example, a gain of 1, and substantially only frequency components having a specific frequency or higher are amplified with corresponding gains.

Figure 5:
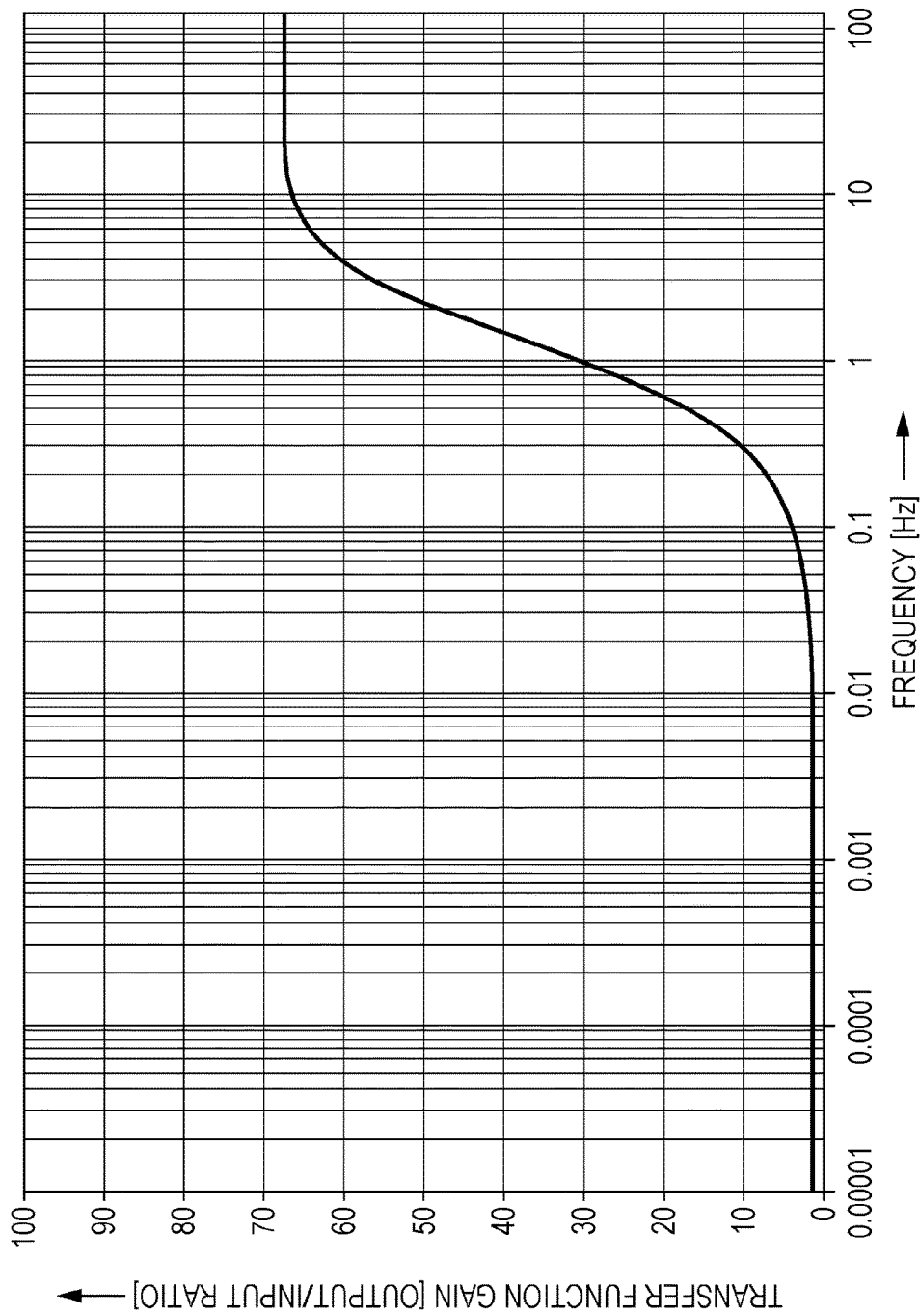
FIG. 5 is a graph illustrating the frequency characteristics of the gain observed when the discrete-time amplifier circuit in FIG. 1 has a 1024 Hz clock frequency.

FIG. 5 is a graph illustrating the frequency characteristics of the gain observed when the amplifier circuit 20 in FIG. 1 has a 1024 Hz clock frequency. As clear from FIG. 5, in the amplifier circuit 20, the direct-current component is hardly amplified with, for example, a gain of 1, and substantially only frequency components having a specific frequency or higher are amplified with corresponding gains. In addition, if the clock frequency is changed, the frequency characteristics of the amplifier circuit 20 can be changed.

With the amplifier circuit 20 according to the embodiment as described above, adjusting the capacitance values and the clock frequencies of the respective capacitors 31, 32, 33, 41, and 22 enables only the alternating-current component to be amplified with the direct-current component being maintained. The amplifier circuit 20 can also be operated intermittently and be operated with lower power consumption than that in the related art. Further, since the pulse-wave measuring device 101 according to this embodiment includes the amplifier circuit 20, an amount of light from the light source and the amplification factor of the amplifier circuit can be determined with lower power consumption than that in the related art. Accordingly, the pulse-wave measuring device 101 has improved detectivity. The intermittent operations of the pulse-wave measuring device 101 according to this embodiment can also lead to improved device operating time.

Embodiment 2

Figure 2:
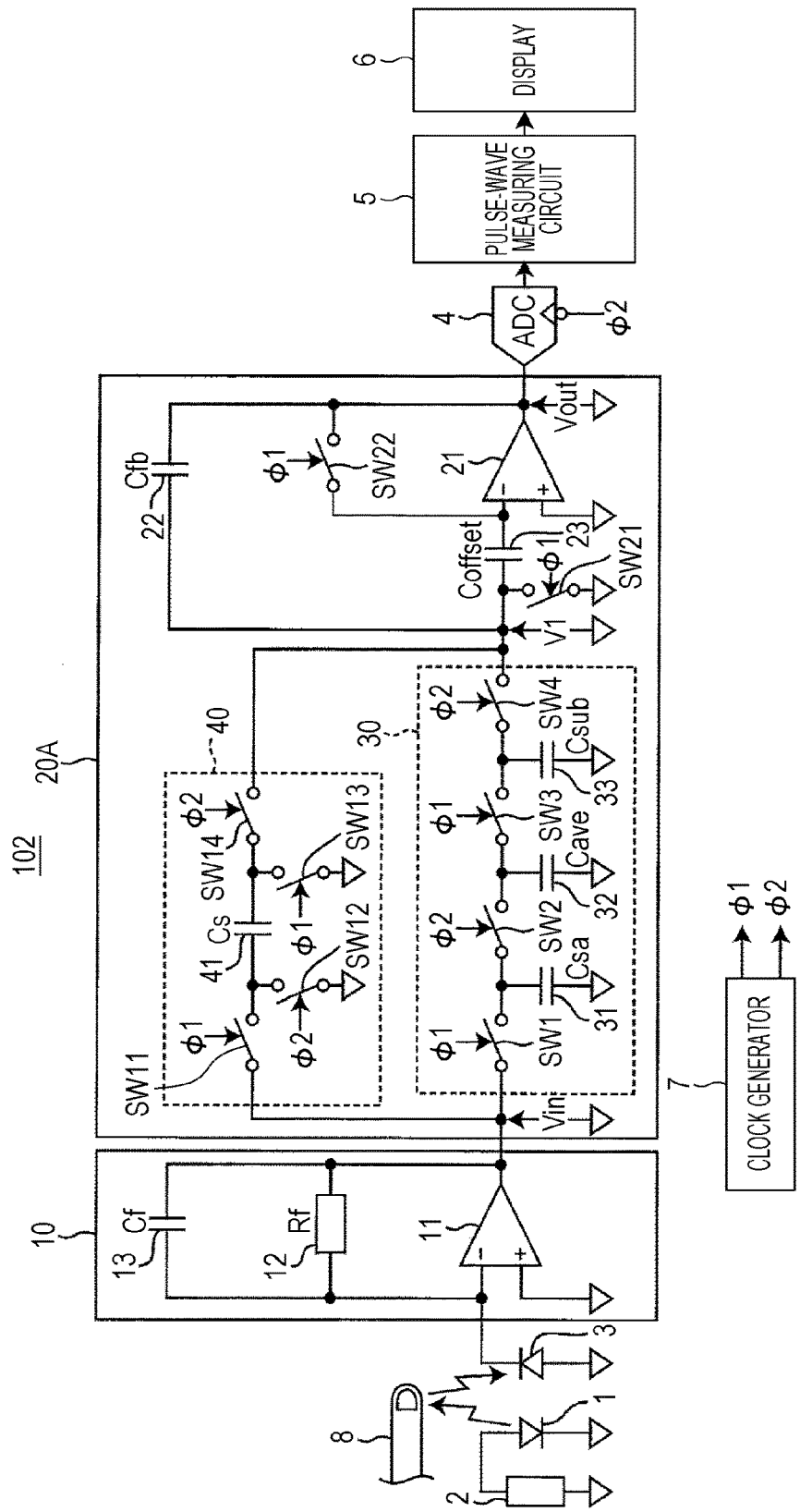
FIG. 2 is a circuit diagram illustrating a configuration example of a blood-vessel pulse-wave measuring device according to Embodiment 2.

FIG. 2 is a circuit diagram illustrating a configuration example of a pulse-wave measuring device 102 according to Embodiment 2. Compared with the pulse-wave measuring device 101 in FIG. 1, the pulse-wave measuring device 102 according to Embodiment 2 in FIG. 2 is characterized by including an amplifier circuit 20A instead of the amplifier circuit 20. The amplifier circuit 20A is a discrete-time amplifier circuit.

Compared with the amplifier circuit 20, the amplifier circuit 20A further includes
(1) a switch SW21 that operates based on the clock signal ϕ1 and resets the voltage V1 to a ground voltage in the first time period, and
(2) an offset capacitor 23 that is inserted between the inverting input terminal of the operational amplifier 21 and the connection between the switch SW21 and the capacitor 22 and has a capacitance value Coffset. The switch SW21 corresponds to a first offset switch in the present disclosure.

The amplifier circuit 20A according to Embodiment 2 configured as described above includes the offset capacitor 23 and thereby has an offset cancellation function and an offset voltage holding function. Charges corresponding to the offset voltage are held in the offset capacitor 23 between the inverting input terminal of the operational amplifier 21 and the connection between the switch SW21 and the capacitor 22 in a period when the clock signal ϕ1 is at the high level. Subsequently, when amplifying the voltage V1 in a period when the clock signal ϕ2 is at the high level, the operational amplifier 21 also amplifies the charges held in the offset capacitor 23. The operational amplifier 21 subtracts the offset voltage from the voltage V1 and amplifies the resultant voltage. The operational amplifier 21 can thereby cancel the influence by the aforementioned offset voltage. Accordingly, the amplifier circuit 20A according to Embodiment 2 can amplify a voltage with higher accuracy compared with Embodiment 1. Note that the pulse-wave measuring device 102 according to Embodiment 2 exerts not only this advantageous effect, but also the same operations and effects as those in Embodiment 1.

Embodiment 3

Figure 3:
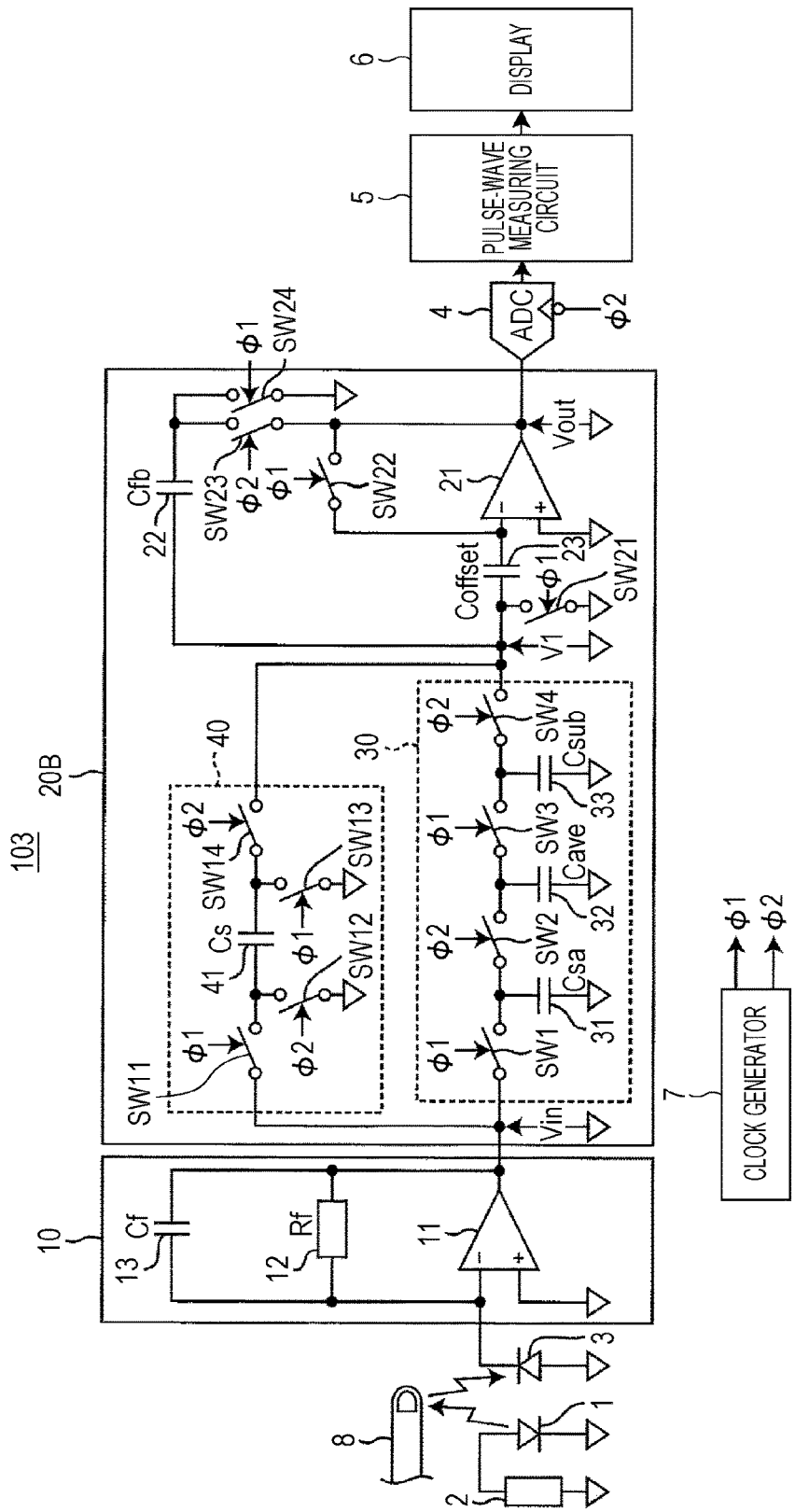
FIG. 3 is a circuit diagram illustrating a configuration example of a blood-vessel pulse-wave measuring device according to Embodiment 3.

FIG. 3 is a circuit diagram illustrating a configuration example of a pulse-wave measuring device 103 according to Embodiment 3. Compared with the pulse-wave measuring device 102 in FIG. 2, the pulse-wave measuring device 103 according to Embodiment 3 in FIG. 3 is characterized by including an amplifier circuit 20B instead of the amplifier circuit 20A. The amplifier circuit 20B is a discrete-time amplifier circuit.

Compared with the amplifier circuit 20A, the amplifier circuit 20B further includes
(1) an offset switch SW23 that is inserted between the output terminal of the operational amplifier 21 and the capacitor 22, operates in accordance with the clock signal ϕ2, are switched off in the first time period, and are switched on in the second time period, and
(2) an offset switch SW24 that is inserted between the switch SW23 and the ground, operates in accordance with the clock signal ϕ1, is switched on in the first time period, and is switched off in the second time period. The switch SW23 and the switch SW24 respectively correspond to a second offset switch and a third offset switch in the present disclosure.

Accordingly, the switches SW21 and SW24 are on in the first time period. Both ends of the feedback capacitor 22 are grounded, and the charges are released.

The amplifier circuit 20B according to Embodiment 3 configured as described above includes the offset capacitor 23 and thereby has the offset cancellation function and the offset voltage holding function. Accordingly, the amplifier circuit 20B according to Embodiment 3 can amplify a voltage with higher accuracy compared with Embodiments 1 and 2. Note that the pulse-wave measuring device 103 according to Embodiment 3 exerts not only this advantageous effect, but also the same operations and effects as those in Embodiments 1 and 2.

Note that the amplifier circuits 20, 20A, and 20B may each be composed of, for example, a semiconductor circuit or a semiconductor integrated circuit.

What is claimed is:

1. An amplifier circuit comprising:
   a first input branch circuit including a first sampling capacitor that, in operation, samples an input voltage in a first time period and outputs a first voltage;
   a second input branch circuit including a second sampling capacitor, an averaging capacitor, and a subtraction capacitor, the second sampling capacitor, in operation, sampling the input voltage in the first time period and outputting a second voltage, the averaging capacitor, in operation, taking an average of the second voltage in the second time period and outputting a third voltage, the subtraction capacitor, in operation, receiving the third voltage in the first time period, the subtraction capacitor, in operation, subtracting the first voltage from the third voltage and outputting a fourth voltage in the second time period;
   a feedback capacitor; and
   an operational amplifier that is connected to the feedback capacitor and, in operation, amplifies the fourth voltage,
   wherein the first time period and the second time period are repeated alternately.

2. The amplifier circuit according to claim 1, further comprising:
   an offset capacitor inserted between the second input branch circuit and an input terminal of the operational amplifier; and
   a first offset switch that is inserted between a ground and a connection between the second input branch circuit and the offset capacitor, is switched on in the first time period, and is switched off in the second time period,
   wherein a noninverting input terminal of the operational amplifier is grounded.

3. The amplifier circuit according to claim 2, further comprising:
   a second offset switch that is inserted between an output terminal of the operational amplifier and the feedback capacitor, is switched off in the first time period, and is switched on in the second time period; and
   a third offset switch that is inserted between the feedback capacitor and the ground, is switched on in the first time period, and is switched off in the second time period.

4. The amplifier circuit according to claim 1, wherein:
   a capacitance value of the first sampling capacitor is set to be equal to a total capacitance value of the second sampling capacitor, the averaging capacitor, the subtraction capacitor, and the feedback capacitor,
   the second sampling capacitor, the averaging capacitor, and the subtraction capacitor are connected together in series, and
   the feedback capacitor is connected to the second sampling capacitor, the averaging capacitor, and the subtraction capacitor in parallel.

5. The amplifier circuit according to claim 1, wherein:
   a capacitance value of the first sampling capacitor is set to be equal to a total capacitance value of the second sampling capacitor, the subtraction capacitor, and the feedback capacitor,
   the second sampling capacitor and the subtraction capacitor are connected together in series, and
   the feedback capacitor is connected to the second sampling capacitor and the subtraction capacitor in parallel.

6. A pulse-wave measuring device comprising:
   a light source;
   a photodetector that, in operation, detects light from a target and outputs current;
   a current-voltage conversion circuit that, in operation, converts the current to a voltage and outputs the voltage;
   an amplifier circuit that, in operation, amplifies the voltage output by the current-voltage conversion circuit at a discrete time and outputs an analog voltage; and
   an analog-to-digital converter that, in operation, converts the analog voltage to a digital voltage, wherein:
   the amplifier circuit includes
   a first input branch circuit including a first sampling capacitor that, in operation, samples the voltage output by the current-voltage conversion circuit in a first time period and outputs a first voltage,
   a second input branch circuit including a second sampling capacitor, an averaging capacitor, and a subtraction capacitor, the second sampling capacitor, in operation, sampling the voltage output by the current-voltage conversion circuit in the first time period and outputting a second voltage, the averaging capacitor, in operation, taking an average of the second voltage in the second time period and outputting a third voltage, the subtraction capacitor, in operation, receiving the third voltage in the first time period, the subtraction capacitor, in operation, subtracting the first voltage from the third voltage and outputting a fourth voltage in the second time period,
   a feedback capacitor, and
   an operational amplifier that is connected to the feedback capacitor and, in operation, amplifies the fourth voltage, and the first time period and the second time period are repeated alternately.

\* \* \* \* \*